(12) United States Patent
Aebischer et al.

(10) Patent No.: US 6,235,511 B1
(45) Date of Patent: May 22, 2001

(54) **COMPOSITIONS PREPARED TO CONTAIN ACTIVE DEXTRAN SUCRASE PRODUCED BY *LEUCONOSTOC MESENTEROIDES* SSP. *CREMORIS***

(75) Inventors: Jürg Aebischer, Niederschärli; Nicola D'Amico, Treycovagnes; Dominique De Maleprade, Vevey; Kurt Eyer, Thun, all of (CH); Corinne Lesens, Beauvais (FR); Jean-Richard Neeser, Savigny (CH); Roberto Reniero, Le Mont-Pelerin (CH); Daniel Schmid, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/439,005

(22) Filed: Nov. 12, 1999

Related U.S. Application Data

(62) Division of application No. 09/087,643, filed on May 29, 1998, now Pat. No. 6,004,800.

(30) Foreign Application Priority Data

May 31, 1997 (EP) .................................................. 97201628

(51) Int. Cl.[7] ...................................................... C12N 9/10
(52) U.S. Cl. ........................ 435/193; 435/200; 435/211; 435/101; 435/103; 536/112; 424/94.61; 426/56
(58) Field of Search ......................... 424/94.61; 426/56; 435/193, 200, 211, 101, 103; 536/112

(56) References Cited

U.S. PATENT DOCUMENTS

| 4,933,191 | 6/1990 | Pucci et al. | ........................... 426/48 |
| 5,223,431 | 6/1993 | Pucci et al. | ....................... 435/252.9 |

FOREIGN PATENT DOCUMENTS

| 0363633 | 4/1990 | (EP) | ............................... C12P/19/08 |

OTHER PUBLICATIONS

Levata–Jovanovic, et al., "Citrate Utilization and Diacetyl Production by Various Strains of *Leuconostoc mesenteroides* ssp. *cremoris*" 1996 J. Dairy Sci. 79:1928–1935.

Schmitt et al., "Origin of end–products from the co–metabolism of glucose and citrate by *Leuconostoc mesenteroides* subsp. *cremoris*", Appl. Microbiol. biotechnol. (1992) 36:679–683.

Milliere, et al., "Phenotypic characterization of Leuconostoc species", *Journal of Applied Bacteriology* 1989, 63, 551–558.

Cogan, "Co–metabolism of citrate and glucose by Leuconostoc spp.: effects on growth, substrates and products", *Journal of Applied Bacteriology* 1987, 63, 551–558.

Garvie, "*Leuconostoc mesenteroides* subsp. *cremoris* (Knudsen and Sørensen) comb. nov. and *Leuconostoc mesenteroides* subsp. dextranicum (Beijerinck) comb. nov.", International Journal of Systematic Bacteriolgy, Jan. 1983, pp. 118–119.

Lawford, et al., "Dextran Biosynthesis and Dextransucrase prodution by Continuous Culture of *Leuconostoc mesenteroides*", Biotechnology and Bioengineering, vol. XXI, pp. 1121–1131 (1979).

Database Abstract, Derwent Information Ltd., WPI Accesion No. 96–365593/199637, abstract of Japanese Patent Document JP–A–8 173 178.

Database Abstract, Derwent Information Ltd., WPI Accesion No. 95–287986/199538, abstract of Japanese Patent Document JP–A 184 687 (1995).

*Primary Examiner*—Francisco Prats
(74) *Attorney, Agent, or Firm*—Vogt & O'Donnell, LLP

(57) ABSTRACT

A food or cosmetic composition containing active dextran sucrase enzymes which are produced by a strain of *Leuconostoc mesenteroides* ssp. *cremoris* and which synthesize dextran. In addition to culturing the strain in a food or cosmetic composition containing sucrose to obtain a composition containing the active enzymes, the strain may be cultured in a culture medium containing sucrose to obtain a culture product containing the active dextran sucrase enzymes which may be isolated from the culture product and incorporated into a food or cosmetic substance.

23 Claims, No Drawings

COMPOSITIONS PREPARED TO CONTAIN ACTIVE DEXTRAN SUCRASE PRODUCED BY *LEUCONOSTOC MESENTEROIDES* SSP. *CREMORIS*

CROSS-REFERENCE TO RELATED APPLICATION

This application is a divisional application of application Ser. No. 09/087,643 which was filed May 29, 1998 and which issued as U.S. Pat. No. 6,004,800.

BACKGROUND OF THE INVENTION

The present invention relates to dextran sucrase produced by bacteria and means for production of the same and its use.

STATE OF THE ART

Dextran is a polysaccharide formed of glucose units, the chain lengthening of which is catalyzed by dextran sucrase. The biosynthesis of dextran has been demonstrated in numerous bacteria, especially in *Streptococcus mutans, Leuconostoc mesenteroides* ssp. *mesenteroides* and *Leuconostoc mesenteroides* ssp. *dextranicum*. Leuconostoc produce the enzyme dextran sucrase and secrete it into the culture medium in the presence of sucrose. This enzyme, dextran sucrase, then synthesizes dextran from the sucrose substrate. Dextran has applications in several fields. It is used especially in biochemistry as a support for filtration chromatography on a gel of the Sephadex type. Additionally, in the field of therapeutics, it is used as a substitute for blood plasma (Biochimie générale (General Biochemistry)—J. H. WEIL—Masson, 6th edition—1990—p. 171).

Furthermore, dextran synthesized by a strain of *Leuconostoc dextranicum* is applied in the food industry for the texturing of food products such as yoghurts, cream desserts, milk-based drinks and salad dressings. European Patent Application Publication No. EP 0 363 633 demonstrates the synthesis of dextran by a strain of *Leuconostoc dextranicum* and in particular by the strain *Leuconostoc dextranicum* NRRL-B-18242. Additionally, that patent application publication describes especially a composition containing dextran synthesized by this bacterium and the use of this composition in the food sector.

Moreover, the taxonomy of the bacterial strains of the genus Leuconostoc has been revised several times.

Garvie et al. (International Journal of Systematic Bacteriology, 118–119, 1983) describe the taxonomy of the bacterial strains of the genus Leuconostoc, established according to a criterion of homology in terms of the deoxyribonucleic acid (DNA). The bacteria, previously classed as *Leuconostoc mesenteroides, Leuconostoc dextranicum* and *Leuconostoc cremoris,* although of different phenotype, have a very high degree of homology in respect of their DNA. Therefore, according to this taxonomy, these bacteria are subspecies of *Leuconostoc mesenteroides* and are respectively called *Leuconostoc mesenteroides* ssp. *mesenteroides, Leuconostoc mesenteroides* ssp. *dextranicum* and *Leuconostoc mesenteroides* ssp. *cremoris*.

In addition, J. B. Milliere et al. (Journal of Applied Bacteriology, 67, 529–542, 1989) describe a taxonomic analysis performed on 81 strains of the genus Leuconostoc, including 11 strains of *Leuconostoc mesenteroides* ssp. *cremoris*. This analysis relies on the taxonomy established by Garvie et al. and is based on the following criteria in particular: the capacity of these strains to ferment various sugars, the capacity of these strains to utilize citrate and the capacity of these strains to produce dextran. This document notes the fact that a strain of *Leuconostoc mesenteroides* ssp. *cremoris* does not synthesize dextran. Also, such a strain is distinguished and defined by the fact that it does not ferment pentoses.

No strain of *Leuconostoc mesenteroides* ssp. *cremoris* has yet been isolated which is capable of synthesizing dextran. Now, *Leuconostoc mesenteroides* ssp. *cremoris* is of major importance in the manufacture of dairy products such as, for example, yoghurt-type fermented specialities or dairy creams. It would therefore be very valuable to be able to use such bacteria, capable of synthesizing dextran of pleasant texture and taste, especially for texturing this type of food product.

The object of the present invention is to meet this need.

SUMMARY OF THE INVENTION

For meeting the need noted above the present invention provides strains of *Leuconostoc mesenteroides* ssp. *cremoris* which produce dextran, especially the strains *Leuconostoc mesenteroides* ssp. *cremoris* CNCM I-1692 and CNCM I-1693.

The present invention further provides a method of using a strain of *Leuconostoc mesenteroides* ssp. *cremoris* for the manufacture of a food product or cosmetic composition.

The present invention further provides a process for the production of dextran from *Leuconostoc mesenteroides* ssp. *cremoris*.

The present invention further provides a food composition or cosmetic composition into which dextran obtained by carrying out the process is incorporated during its preparation.

The present invention further provides a process for the production of an additive containing active dextran sucrase from *Leuconostoc mesenteroides* ssp. *cremoris*.

The present invention finally relates to a food product or cosmetic composition which contains active dextran sucrase produced by *Leuconostoc mesenteroides* ssp. including a composition into which an additive containing active dextran sucrase from *Leuconostoc mesenteroides* ssp. *cremoris* is incorporated during its preparation.

DETAILED DESCRIPTION OF THE INVENTION

As described above, present invention provides strains of *Leuconostoc mesenteroides* ssp. *cremoris* which produce dextran. It was possible to isolate strains of *Leuconostoc mesenteroides* ssp. *cremoris* which produce dextran. All the strains of *Leuconostoc mesenteroides* ssp. *cremoris* which produce dextran are therefore covered by the present invention.

A strain of *Leuconostoc mesenteroides* ssp. *cremoris* was isolated particularly from a Swiss cream and it was found, surprisingly, to have the remarkable property of synthesizing dextran of pleasant texture and taste. This strain was deposited on Apr. 18, 1996, under the terms of the Budapest Treaty, in the Collection National de Cultures de Microorganismes, INSTITUT PASTEUR, 25, rue du Docteur Roux, F-75724 PARIS CEDEX 15, where it was given the deposit number CNCM I-1692.

Furthermore, a strain of *Leuconostoc mesenteroides* ssp. *cremoris* which also has the remarkable property of synthesizing dextran of pleasant texture and taste was isolated by natural selection from the strain CNCM I-1692. This strain was deposited on Apr. 4, 1996, under the terms of the Budapest Treaty, in the Collection Nationale de Cultures de Microorganismes, INSTITUT PASTEUR, 25, rue du Docteur Roux, F-75724 PARIS CEDEX 15, where it was given the deposit number CNCM I-1693.

Details of these strains, concerning especially their morphology, the fermentation of sugars and other aspects, are given below.

Morphology
- Gram-positive microorganisms,
- Negative catalase,
- Facultative aerobe, and
- Cocci.

Fermentation of Sugars
- No lactic acid production from pentoses, D- and L-arabinose, D- and L-xylose and D- and L-ribose,
- Lactic acid production from lactose by the strain CNCM I-1692, and
- No lactic acid production from lactose by the strain CNCM I-1693.

Other Aspects
- Strains synthesizing dextran, a polysaccharide with remarkable texturing properties.

According to the present invention, it is therefore possible also to isolate a strain of Leuconostoc mesenteroides ssp. cremoris which does not ferment lactose, an example being CNCM I-1693.

A preferred strain according to the present invention produces the same dextran as the strain CNCM I-1692 or the strain CNCM I-1693.

As indicated above, present invention provides a process for the production of dextran wherein a medium containing sucrose is inoculated with a preculture of a strain of Leuconostoc mesenteroides ssp. cremoris according to the invention, it is allowed to ferment at 25–35° C. for 10–20 h and the pH of the resulting culture is then lowered to 5–5.5 prior to storage at 0–10° C. for 16–48 h.

A medium containing at least 2% of sucrose can be inoculated with a preculture of a strain of Leuconostoc mesenteroides ssp. cremoris according to the invention, for example in order to allow the production of dextran sucrase and the synthesis of dextran in the culture medium.

A medium containing 5–12% of MSK medium (skimmed cow's milk) supplemented with 0.05–0.2% of yeast extract and at least 2% of sucrose, for example, can be inoculated with 0.2–3% of a preculture of a strain of Leuconostoc mesenteroides ssp. cremoris according to the present invention, particularly the strain CNCM I-1692 or the strain CNCM I-1693. The medium can be allowed to ferment at 25–35° C. for 10–20 h with the pH being maintained at 6–7.3, for example. Then, when fermentation has ended, the pH of the resulting culture can be lowered to 5–5.5 by the addition of lactic acid, for example. The culture is then stored at 0–10° C. for 16–48 h.

Also, a medium containing 0.05–0.2% of yeast extract with at least 2% of sucrose, for example, can be inoculated with 0.2–3% of a preculture of a strain of Leuconostoc mesenteroides ssp. cremoris according to the present invention, particularly the strain CNCM I-1692 or the strain CNCM I-1693. The medium can be allowed to ferment at 25–35° C. for 10–20 h with the pH being maintained at 6–7.3, for example. When fermentation has ended, this culture can be mixed with an equal volume of 20% MSK medium so that inhibition of the production of the enzyme dextran sucrase by the lactose contained in the MSK medium, for example, is avoided during the fermentation. The pH of the resulting culture can then be lowered to 5–5.5 by the addition of lactic acid, for example. The culture is then stored at 0–10° C. for 16–48 h.

This culture can then be dried to give a dextran powder, for example. This culture can be dried by lyophilization or spray drying, for example.

As indicated above, present invention further provides a food product or cosmetic composition comprising dextran from Leuconostoc mesenteroides ssp. cremoris which is obtainable by carrying out the above process.

To prepare such a product or composition, dextran obtained by carrying out the above process for the production of dextran can be incorporated into a food or cosmetic product, such as a milk powder, a yoghurt, a ketchup, a mayonnaise or a skin cream, during its manufacture, for example.

As also indicated above, present invention further provides a process for the production of an additive containing active dextran sucrase wherein a medium containing sucrose is inoculated with a preculture of a strain of Leuconostoc mesenteroides ssp. cremoris according to the invention and is then allowed to ferment at 25–35° C. for 10–20 h.

A medium containing at least 2% of sucrose can be inoculated with a preculture of a strain of Leuconostoc mesenteroides ssp. cremoris according to the invention in order to allow the production of dextran sucrase in the culture medium, for example.

A medium containing 5–12% of MSK medium (skimmed cow's milk) supplemented with 0.05–0.2% of yeast extract and at least 2% of sucrose, for example, can be inoculated with 0.2–3% of a preculture of a strain of Leuconostoc mesenteroides ssp. cremoris according to the present invention, particularly with 0.2–3% of a preculture of the strain CNCM I-1692 or the strain CNCM I-1693. It can be allowed to ferment at 25–35° C. for 10–20 h with the pH being maintained at 6–7.3, for example.

A medium containing 0.05–0.2% of yeast extract and at least 2% of sucrose, for example, can be inoculated with 0.2–3% of a preculture of a strain of Leuconostoc mesenteroides ssp. cremoris according to the present invention, particularly with 0.2–3% of a preculture of the strain CNCM I-1692 or the strain CNCM I-1693. It can be allowed to ferment at 25–35° C. for 10–20 h with the pH being maintained at 6–7.3, for example. When fermentation has ended, this culture can be mixed with an equal volume of 20% MSK medium so that inhibition of the production of the enzyme dextran sucrase by the lactose contained in the MSK medium, for example, can be avoided during the fermentation.

Also, a synthetic culture medium containing at least 2% of sucrose, 1–3% of $K_2HPO_4$, 0.2–1% of yeast extract, 0.2–1% of peptone and 0.0005–0.001% of $MnSO_4$ can be inoculated with 0.2–3% of a preculture of a strain of Leuconostoc mesenteroides ssp. cremoris according to the present invention, particularly with 0.2–3% of a preculture of the strain CNCM I-1692 or the strain CNCM I-1693. It can be allowed to ferment at 25–35° C. for 7–12 h with the pH being maintained at 6–7.3, for example.

In a first preferred embodiment of the process for the preparation of an additive containing active dextran sucrase, the pH of the culture is adjusted to 5–5.5 after fermentation and this culture is then dried to give a powder containing the active dextran sucrase. The pH of the culture can be adjusted by the addition of lactic acid, for example. The culture can be dried by lyophilization or by spray drying, for example.

In a second preferred embodiment of the process for the preparation of active dextran sucrase, the culture is separated after fermentation so as to isolate the supernatant containing the active dextran sucrase. This separation can be effected by centrifugation at 15,000–20,000 g for 10–35 min at 2–6° C., for example.

It is possible to adjust the pH of the supernatant to 4.9–5.7, store this supernatant at 0–10° C. for 15–30 h and then precipitate the macromolecules contained in this supernatant so as to isolate a precipitate containing the dextran sucrase, for example. The macromolecules in the supernatant can be precipitated with polyethylene glycol or ammonium sulphate at 2–6° C., with stirring, for example.

The precipitate containing the dextran sucrase can then be dialyzed so as to eliminate the precipitating agents, for example.

Finally, in this second preferred embodiment of the present process, the precipitate containing the dextran sucrase can be stored at a temperature below −4° C. after the precipitation step or after the dialysis step, for example.

As indicated above, present invention further provides a food product or cosmetic composition comprising an additive containing active dextran sucrase from *Leuconostoc mesenteroides* ssp. *cremoris* obtainable by carrying out the above process.

To prepare such a product or composition, an additive containing active dextran sucrase obtained in this way can be incorporated into a food or cosmetic product, such as a milk powder, a yoghurt, a ketchup, a mayonnaise or a skin cream, during its manufacture, for example.

Finally, the present invention further provides to a method of using a strain of *Leuconostoc mesenteroides* ssp. *cremoris* according to the present invention for the manufacture of a food product or cosmetic composition.

The strains of *Leuconostoc mesenteroides* ssp. *cremoris*, the dextran sucrase produced by these strains and the dextran synthesized by these strains according to the present invention are characterized in greater detail below by means of different microbiological and biochemical data illustrating their properties. The percentages are given by weight, unless indicated otherwise.

METHODOLOGIES

Testing for the Strains of Leuconostoc which Produce Dextran

Tests for the strains which produce dextran were performed on 150 strains isolated either from dairy products or from non-dairy products such as wine, coffee and sauerkraut.

The production of dextran in a medium containing sucrose is measured.

To do this, 10 ml of DEX medium comprising 1% of *B. tryptone*, 0.5% of yeast extract, 0.5% of $K_2HPO_4$, 0.5% of ammonium citrate and 5% of sucrose are inoculated with 1% of a preculture of each of the 150 strains. The medium is then allowed to ferment at 30° C. for 24 h.

16 strains capable of producing dextran were thus selected from the 150 starting strains.

150 ml of DEX medium, as described above, are then inoculated with 1% of a preculture of each of these 16 selected strains and then allowed to ferment at 30° C. for 24 h prior to measurement of the viscosity of the product of these 16 cultures obtained in this way. The viscosity is measured with a gravity viscometer of diameter 25 mm.

Table I below shows the values in seconds for the passage of 100 ml of the product of each culture through the gravity viscometer. The strain A1, shown in Table I, was used as a negative control strain.

In Table I, the strains A are strains of Leuconostoc sp., the strains B are strains of *Leuconostoc mesenteroides* ssp. *cremoris*, the strain C1 is a strain of *Leuconostoc lactis* and the strains D are strains of *Leuconostoc mesenteroides* spp. *mesenteroides*.

TABLE I

| Strain | Viscosity (s) |
| --- | --- |
| A1 | 11 |
| A2 | 16 |
| A3 | 14 |
| A4 | 13 |
| A5 | 18 |
| A6 | 20 |
| A7 | 19 |
| A8 | 19 |
| C1 | 17 |

TABLE I-continued

| Strain | Viscosity (s) |
| --- | --- |
| CNCM I-1692 | 22 |
| B1 | 12 |
| B2 | 14 |
| B3 | 15 |
| D1 | 12 |
| D2 | 14 |
| D3 | 15 |
| D4 | 17 |

The results shown in Table I demonstrate the fact that the strain *Leuconostoc mesenteroides* ssp. *cremoris* CNCM I-1692 has the highest viscosity of the 16 selected strains, so it is acknowledged that the strain *Leuconostoc mesenteroides* ssp. *cremoris* CNCM I-1692 produces the greatest amount of dextran.

Study of the Concentration of the Enzyme Dextran Sucrase as a Function of Fermentation Time A synthetic medium containing 2% of sucrose, 2% of $K_2HPO_4$, 0.5% of yeast extract, 0.5% of peptone, 0.02% of $MgSO_4$, 0.001% of $MnSO_4$, 0.001% of $FeSO_4$ and 0.001% of NaCl is inoculated with 1% of a preculture of the strain *Leuconostoc mesenteroides* ssp. *cremoris* CNCM I-1692. It is allowed to ferment at 30° C. for 12 h in a 5 l fermenter.

After 4 h of fermentation, a sample of the resulting culture is taken every 2 hours, up to a fermentation time of 12 h, for measurement of the growth of the strain by means of the optical density at 600 nm.

Each sample is then centrifuged at 18,000 g for 20 min at 4° C., the supernatant is recovered, its pH is adjusted to 5.2 and the activity of the dextran sucrase contained in the supernatant is verified by measurement of the incorporation of radioactivity into the dextran from radioactive sucrose (J. Dent. Res. 1974, 53, 1355–1360).

Table II shows the results obtained for measurement of the growth of the strain on the basis of samples taken every 2 hours between fermentation times of 4 and 12 h. Table II also shows the results of measurement of the activity of the dextran sucrase contained in the supernatant of these samples.

TABLE II

| fermentation time (h) | 4 | 6 | 8 | 10 | 12 |
| --- | --- | --- | --- | --- | --- |
| growth $(OD_{600})/10$ | 0.034 | 0.085 | 0.21 | 0.51 | 0.53 |
| activity (u/ml) | — | 0.1 | 0.17 | 0.6 | 0.61 |

The results given in Table II demonstrate the fact that the concentration of dextran sucrase reaches its maximum value just after the *Leuconostoc mesenteroides* ssp. *cremoris* bacteria enter the stationary phase.

Purification of the Enzyme Dextran Sucrase and Determination of its Specific Activity A culture medium containing 0.2% of sucrose, 0.5% of yeast extract, 0.5% of peptone, 2% of $K_2HPO_4$, 0.02% of $MgSO_4$, 0.001% of $MnSO_4$, 0.001% of $FeSO_4$ and 0.001% of NaCl is inoculated with 1% of a preculture of *Leuconostoc mesenteroides* ssp. *cremoris* CNCM I-1692 and allowed to ferment at room temperature for 12 h with the pH being maintained at a value of 6.7.

The culture prepared in this way is then centrifuged at 18,000 g for 20 min at 4° C.

The supernatant containing the dextran sucrase is then isolated and its pH is adjusted to a value of 5.2 prior to incubation for 4 h at 4° C.

The supernatant is then mixed with an equal volume of 33% polyethylene glycol 400 and the mixture is allowed to incubate at 4° C. for 5 h, with stirring, so as to precipitate the proteins contained in the supernatant.

The mixture is centrifuged at 18,000 g for 20 min at 40° C. so as to isolate the residue containing the precipitated proteins.

This residue containing the precipitated proteins is then suspended in 70 ml of 20 mM ammonium acetate, pH 5.2.

600μg of dextranase are then added to this suspension and the whole is allowed to incubate at 25° C. for 1 h so that the dextran contained in the suspension is digested by the dextranase.

The suspension is dialyzed in the presence of 70 ml of 20 mM ammonium acetate, pH 5.2, so as to eliminate the glucose molecules obtained after digestion of the dextran with the dextranase. The proteins are then isolated on an anion exchange column (Fast Q, Pharmacia Biotech AB, Uppsala, SU) which has been equilibrated beforehand with a 20 mM ammonium acetate buffer, pH 5.2.

The proteins are eluted over a linear gradient of 0–0.5 M NaCl.

The activity of the dextran sucrase in the different protein fractions eluted in this way is analyzed and these protein fractions are subjected to electrophoresis on an SDS-polyacrylamide gel.

The protein fractions containing the dextran sucrase are isolated and the activity of the purified dextran sucrase is measured and found to be 105 u/mg.

Texturing Capacity of the Dextrans as a Function of the Incubation Temperature of the Enzyme The activity of the dextran sucrase from the strain *Leuconostoc mesenteroides* ssp. *cremoris* CNCM I-1692 is demonstrated, on the one hand at 30° C. and on the other hand at 4° C., thereby verifying the texturing capacity of the dextrans at these different temperatures.

This is done by preparing an additive containing active dextran sucrase from a culture of the strain *Leuconostoc mesenteroides* ssp. *cremoris* CNCM I-1692.

A synthetic medium containing 2% of sucrose, 2% of $K_2HPO_4$, 0.5% of yeast extract, 0.5% of peptone, 0.02% of $MgSO_4$, 0.001% of $MnSO_4$, 0.001% of $FeSO_4$ and 0.001% of NaCl is inoculated with 1% of a preculture of the strain *Leuconostoc mesenteroides* ssp. *cremoris* CNCM I-1692. It is allowed to ferment at 30° C. for 12 h with the pH being maintained at 6.7.

The culture is then separated by centrifugation at 18,000 g for 20 min at 4° C. so as to isolate the supernatant containing the dextran sucrase.

The pH of the supernatant is lowered to 5.2 and this supernatant is incubated for 12 h at 4° C.

The macromolecules in the supernatant are then precipitated twice with polyethylene glycol at 4° C. so as to purify the dextran sucrase.

The texturing capacity of the dextrans synthesized by the dextran sucrase isolated in this way is then verified by incubating the latter, on the one hand at 30° C. and on the other hand at 4° C., in a buffer-substrate containing 20 mM acetate, pH 5.2, 200 mM sucrose and 20 mM $CaCl_2$.

Table III shows the results of texturing with the active dextran sucrase from the strain *Leuconostoc mesenteroides* ssp. *cremoris* CNCM I-1692, on the one hand at 30° C. and on the other hand at 4° C.

TABLE III

| medium | incubation conditions | texturing |
| --- | --- | --- |
| a | 30° C. for 12 h | – |
|   | 4° C. for 12 h | +++++ | a: buffer-substrate medium of pH 5.2
–: absence of texture
+++++: good texture, very thick The results shown in Table III demonstrate the fact that the dextran sucrase from the strain *Leuconostoc mesenteroides* ssp. *cremoris* CNCM I-1692 makes it possible at 4° C. to synthesize a dextran with a thick and pleasant texture, whereas at 30° C. a turbid solution devoid of texture is obtained. This difference in texturing is without doubt due to the fact that at 4° C. the dextran is in the form of molecules with short branches and thus makes it possible to obtain a thick and pleasant texture, whereas at 30° C. the dextran is in the form of molecules with long branches aligned parallel with the main chain. These molecules do not afford a good texture.

Texturing of a Dairy Product with the Dextran Sucrase

The dextran sucrase is incubated under conditions (medium, temperature and pH) identical to those which prevail during the preparation of a yoghurt.

This is done by preparing an additive containing active dextran sucrase from a culture of the strain *Leuconostoc mesenteroides* ssp. *cremoris* CNCM I-1692.

A synthetic medium containing 2% of sucrose, 2% of $K_2HPO_4$, 0.5% of yeast extract, 0.5% of peptone, 0.02% of $MgSO_4$, 0.001% of $MnSO_4$, 0.001% of $FeSO_4$ and 0.001% of NaCl is inoculated with 1% of a preculture of the strain *Leuconostoc mesenteroides* ssp. *cremoris* CNCM I-1692. It is allowed to ferment at 30° C. overnight with the pH being maintained at 6.7.

The culture is then separated by centrifugation at 18,000 g for 20 min at 4° C. so as to isolate the supernatant containing the dextran sucrase.

The pH of the supernatant is then lowered to 5.2 and this supernatant is incubated for 12 h at 4° C.

The macromolecules in the supernatant are then precipitated twice with polyethylene glycol at 4° C. so as to purify the dextran sucrase.

The synthesis of dextran by the dextran sucrase is then verified. This is done by incubating the dextran sucrase on the one hand in a buffer-substrate of pH 6.4 containing 20 mM acetate, 200 mM sucrose and 20 mM $CaCl_2$, and on the other hand in a milk drink containing 6% of sucrose.

Table IV below shows the results obtained for texturing with the dextran sucrase from the strain *Leuconostoc mesenteroides* ssp. *cremoris* CNCM I-1692.

TABLE IV

| medium | simulation conditions | texture |
| --- | --- | --- |
| a | c | – |
|   | d | +++++ |
| b | c | + |
|   | d | +++++ | a: buffer-substrate of pH 6.4
b: milk drink containing 6% of sucrose
c: 5 h at 37° C. followed by adjustment of the pH to 4.7, lowering of the temperature to 4° C. and incubation for 24 h at 4° C.
d: 5 h at 20° C. followed by adjustment of the pH to 4.7, lowering of the temperature to 4° C. and incubation for 24 h at 4° C.
–: absence of texture
+: small amount of texture
+++++: good texture The results shown in Table IV make it possible to demonstrate the fact that the dextran sucrase also textures a milk-based medium, but no longer produces thickening dextran after 5 h at 37° C. Yoghurts can be textured by adding the dextran sucrase after fermentation and before storage at 4° C.

EXAMPLES

The Examples below are given in order to illustrate the use of the dextran, the dextran sucrase and/or a strain producing this dextran and this dextran sucrase in the manufacture of a food product or cosmetic composition according to the present invention. The percentages given are by weight, unless indicated otherwise.

Example 1

The strain *Leuconostoc mesenteroides* ssp. *cremoris* CNCM I-1692 according to the present invention is used for the manufacture of yoghurts.

To do this, 1 l of a milk product containing 2.8% of fats and supplemented with 2% of skimmed milk powder and 6% of sucrose is prepared, it is pasteurized at 96° C. for 30 min and its temperature is then lowered to 42° C.

In a parallel operation, a frozen preculture of a non-thickening strain of *Streptococcus thermophilus* and a frozen preculture of a non-viscous strain *Lactobacillus bulgaricus* are reactivated in a sterile MSK culture medium containing 10% of reconstituted milk powder and 0.1% of commercial yeast extract.

A frozen preculture of the strain of *Leuconostoc mesenteroides* ssp. *cremoris* is also reactivated in an MRS culture medium (MRS lactobacilli—Detroit—USA) and then in a sterile MSK culture medium containing 10% of reconstituted milk powder and 0.1% of commercial yeast extract and supplemented with 1% of sucrose.

The pasteurized milk product is then inoculated with 1% of each of these reactivated precultures and this milk product is then allowed to ferment at 37° C. until the pH reaches a value of 4.5.

Yoghurts are produced in this way and stored at 4° C.

These yoghurts, prepared with a strain of *Leuconostoc mesenteroides* ssp. *cremoris*, have an unctuous texture with a pleasant taste, especially after storage for 10 days at 4° C.

Example 2

The additive containing active dextran sucrase according to the present invention is used for the manufacture of yoghurts.

To do this, a synthetic medium containing 2% of sucrose, 2% of $K_2HPO_4$, 0.5% of yeast extract, 0.5% of peptone, 0.02% of $MgSO_4$, 0.001% of $MnSO_4$, 0.001% of $FeSO_4$ and 0.001% of NaCl is inoculated with 1% of a preculture of the strain *Leuconostoc mesenteroides* ssp. *cremoris* CNCM I-1692. It is allowed to ferment at 30° C. for 12 h with the pH being maintained at 6.7. The culture is then separated by centrifugation at 18,000 g for 20 min at 4° C. so as to isolate the supernatant containing the active dextran sucrase. The pH of the supernatant is lowered to 5.2 and the macromolecules in the supernatant are then precipitated at 4° C. with ammonium sulphate so as to isolate a precipitate containing the dextran sucrase. This precipitate is then dialyzed to remove the ammonium sulphate.

1 l of a milk product containing 2.8% of fats and supplemented with 2% of skimmed milk powder and 6% of sucrose is also prepared, it is pasteurized at 96° C. for 30 min and its temperature is then lowered to 42° C.

In a parallel operation, a frozen preculture of a non-thickening strain of *Streptococcus thermophilus* and a frozen preculture of a non-viscous strain of *Lactobacillus bulgaricus* are reactivated in a sterile MSK culture medium containing 10% of reconstituted milk powder and 0.1% of commercial yeast extract.

The-pasteurized milk product is inoculated with 1% of each of the cultures of the two strains and the milk product is then incubated at 37° C. until the pH reaches a value of 4.5.

1% of purified dextran sucrase is then added, with stirring.

Yoghurts are produced in this way and stored at 4° C.

These yoghurts, prepared with the purified dextran sucrase synthesized by *Leuconostoc mesenteroides* ssp. *cremoris*, have an unctuous texture with a pleasant taste, especially after storage for 10 days at 4° C.

Example 3

The additive containing active dextran sucrase according to the present invention is used in powder form for the manufacture of yoghurts.

To do this, a culture medium containing 9% of skimmed milk powder, 0.1% of yeast extract and 2% of sucrose is inoculated with 1% of a preculture of the strain of *Leuconostoc mesenteroides* ssp. *cremoris*. It is allowed to ferment at 30° C. for 20 h with the pH being maintained at 6.7. The culture is mixed with an equal volume of 20% MSK solution. The pH of the resulting culture is then lowered to 5.2 by the addition of lactic acid before the culture is spray-dried to give the additive containing active dextran sucrase in powder form.

1 l of a milk product containing 2.8% of fats and supplemented with 2% of skimmed milk powder and 6% of sucrose is also prepared, it is pasteurized at 96° C. for 30 min and its temperature is then lowered to 42° C.

In a parallel operation, a frozen preculture of a non-thickening strain of *Streptococcus thermophilus* and a frozen preculture of a non-viscous strain of *Lactobacillus bulgaricus* are reactivated in a sterile MSK culture medium containing 10% of reconstituted milk powder and 0.1% of commercial yeast extract.

The pasteurized milk product is inoculated with 1% of each of the cultures of the two strains and the milk product is then incubated at 40° C. until the pH reaches a value of 4.5. 1% of the additive containing the active dextran sucrase is then added in powder form, with stirring.

Yoghurts are produced in this way and stored at 4° C.

These yoghurts, prepared with the additive containing active dextran sucrase in powder form, have an unctuous texture with a pleasant taste, especially after storage for 10 days at 4° C.

Example 4

The additive containing active dextran sucrase according to the present invention is used in powder form for the manufacture of ice creams.

To do this, a culture medium containing 0.5% of yeast extract and at least 2% of sucrose is inoculated with 1% of a preculture of the strain of *Leuconostoc mesenteroides* ssp. *cremoris*. It is allowed to ferment at 23° C. for 20 h with the pH being maintained at 6.7. The pH of the resulting culture is lowered to 5.2 by the addition of lactic acid. The culture is mixed with an equal volume of 20% MSK solution before being spray-dried to give the additive containing active dextran sucrase in powder form.

In another operation, 100 l of an ice cream mixture containing 8% of fats, 10% of non-fat solids, 14% of sucrose, 3% of glucose syrup DE 36–40, 0.3% of emulsifier, monoglyceride and diglyceride are prepared. This mixture has a total dry extract of 35.28%. The mixture prepared in this way is stirred at 60–65° C. for 20 min, homogenized at 210 bar and at 72° C. (rising homogenization—2 stages), pasteurized at 86° C. for 22 sec and then cooled to +4° C. The output of the homo-pasteurization line is 200 l/h.

The mixture is acidified to pH 5.5 with lactic acid. 1% of the additive containing the active dextran sucrase is then added in powder form, with stirring.

The mixture is then matured at +4° C. When mature, the ice cream mixture prepared with the additive containing active dextran sucrase in powder form has an unctuous texture. It is frozen on a freezer at −5° C., with a 95% volume increase, at a counter pressure of 3 bar and with an output of 80 l/h. The ice cream is then stored at −35° C. in a hardening chamber and subsequently at −30° C. or −20° C.

The ice cream prepared with the additive containing active dextran sucrase in powder form has a good textural quality and a pleasant taste. The ice cream obtained in this way gives a good sensation in the mouth. The ice cream is smooth and unctuous. After accelerated ageing the ice cream preserves a good level of textural quality and of creamy sensation in the mouth. The smooth character of the ice cream is preserved well; this can be explained by the cryoprotective property of the dextrans, which then limits excessive growth of the ice crystals.

Example 5

The additive containing active dextran sucrase according to the present invention is used in powder form for the manufacture of ice creams.

To do this, a culture medium containing 0.5% of yeast extract and at least 2% of sucrose is inoculated with 1% of a preculture of the strain of *Leuconostoc mesenteroides* ssp. *cremoris*. It is allowed to ferment at 23° C. for 20 h with the pH being maintained at 6.7. The pH of the resulting culture is lowered to 5.2 by the addition of lactic acid. The culture is mixed with an equal volume of 20% MSK solution before being spray-dried to give the additive containing active dextran sucrase in powder form.

In another operation, 100 l of a premix containing 18% of sucrose are prepared. 1% of the additive containing the active dextran sucrase is then added in powder form, with stirring. The premix is then incubated at +4° C.

After incubation, the viscosity of the premix has increased. The premix is made up to give a final ice cream mixture containing 8% of fats, 10% of non-fat solids, 14% of sucrose, 3% of glucose syrup DE 36–40, 0.3% of emulsifier, monoglyceride and diglyceride. This mixture has a total dry extract of 35.28%. The mixture prepared in this way is stirred at 60–65° C. for 20 min, homogenized at 210 bar and at 72° C. (rising homogenization—2 stages), pasteurized at 86° C. for 22 sec and then cooled to +4° C. At this point the enzyme is totally inactivated. The output of the homo-pasteurization line is 200 l/h.

The mixture is matured at +4° C. and then frozen on a freezer at −5° C., with a 95% volume increase, at a counterpressure of 3 bar and with an output of 80 l/h. The ice cream is then stored at −35° C. in a hardening chamber and subsequently at −30° C. or −20° C.

The ice cream prepared from a premix incubated with the additive containing active dextran sucrase in powder form has a good textural quality and a pleasant taste. The ice cream obtained in this way gives a good sensation in the mouth. The ice cream is smooth and unctuous. After accelerated ageing the ice cream preserves a good level of textural quality and of creamy sensation in the mouth. The smooth character of the ice cream is preserved well; this can be explained by the cryoprotective property of the dextrans, which then limits excessive growth of the ice crystals.

What is claimed is:

1. A food or cosmetic composition containing active dextran sucrase enzymes which are produced by a strain of *Leuconostoc mesenteroides* ssp. *cremoris* and which synthesize sucrose into a dextran composition.

2. A composition according to claim 1 wherein the strain produces, during culturing in DEX medium, a fermented medium which has, upon passage of 100 ml of the fermented medium through a gravity viscometer having a diameter of 25 mm for determination of viscosity in seconds, a viscosity of at least 12 seconds.

3. A composition according to claim 1 wherein the strain does not ferment lactose.

4. A composition according to claim 2 wherein the strain is selected from the group consisting of isolated bacteria strain *Leuconostoc mesenteroides* ssp. *cremoris* CNCM I-1692 and isolated bacteria strain *Leuconostoc mesenteroides* ssp. *cremoris* CNCM I-1693.

5. A composition according to claim 1 wherein the composition is a food and the food is a yoghurt.

6. A food or cosmetic composition which contains active dextran sucrase enzymes and which is prepared by a process which comprises steps of:

inoculating a medium for culturing bacteria and which comprises sucrose with a culture of a strain of *Leuconostoc mesenteroides* ssp. *cremoris* which produces dextran sucrase enzymes to obtain an inoculated culture medium and incubating the inoculated culture medium at a temperature of from 25° C. to 35° C. for from 10 hours to 20 hours to obtain a fermented medium comprising a substrate and supernatant;

isolating the supernatant from the substrate and recovering the supernatant to obtain a product comprising active dextran sucrase; and incorporating the active dextran sucrase product obtained into a substance selected from the group consisting of a food substance and a cosmetic substance to obtain a composition which contains active dextran sucrase.

7. A composition according to claim 6 wherein, prior to incorporating the active dextran sucrase product into the substance, the process further comprises a step of drying the supernatant to obtain a dried active dextran sucrase product for the incorporating step.

8. A composition according to claim 6 wherein the culture medium is incubated at a pH of from 6 to 7.3 and wherein the process further comprises steps of:

adjusting the pH of the supernatant to a pH of from 4.9 to 5.7 to obtain a pH-adjusted product;

storing the pH-adjusted product at a temperature of from 0° C. to 10° C. for from 15 hours to 30 hours to obtain a cooled pH-adjusted product;

treating the cooled pH-adjusted product to obtain a precipitate and a supernatant;

isolating the precipitate from the supernatant and obtaining the precipitate to obtain the active dextran sucrase product for the incorporating step.

9. A composition according to claim 8 wherein the cooled pH-adjusted product has a temperature of from 2° C. to 6° C. and is treated by adding an agent selected from the group consisting of polyethylene glycol and ammonium sulfate to the cooled pH-adjusted product.

10. A composition according to claim 8 wherein the process further comprises, after isolating and obtaining the precipitate product and prior to the incorporating step, a step of dialing the precipitate product to obtain the active dextran sucrase product for the incorporating step.

11. A composition according to claim 9 and wherein the process further comprises, after isolating and obtaining the precipitate product and prior to the incorporating step, a step of dialyzing the precipitate product for removing the agent from the precipitate to obtain the active dextran sucrase product for the incorporating step.

12. A composition according to claim 6 or 8 or 10 wherein the strain produces, during culturing in DEX medium, a fermented medium which has, upon passage of 100 ml of the fermented medium through a gravity viscometer having a diameter of 25 mm for determination of viscosity in seconds, a viscosity of at least 12 seconds.

13. A composition according to claim 6 or 8 or 10 wherein the strain does not ferment lactose.

14. A composition according to claim 6 or 8 or 10 wherein the strain is selected from the group consisting of isolated bacteria strain *Leuconostoc mesenteroides* ssp. *cremoris* CNCM I-1692 and isolated bacteria strain *Leuconostoc mesenteroides* ssp. *cremoris* CNCM I-1693.

15. A composition according to claim 6 wherein the substance is milk or a food substance which comprises milk.

16. A composition according to claim 6 wherein the culture medium comprises the sucrose in an amount of at least 2% by weight.

17. A process for obtaining active dextran sucrase enzymes suitable for use in a food or cosmetic composition which comprises the steps of:

inoculating a medium for culturing bacteria and which comprises sucrose with a culture of a strain of *Leuconostoc mesenteroides* ssp. *cremoris* which produces dextran sucrase enuymes to obtain an inoculated culture medium and incubating the inoculated culture medium at a temperature of from 25° C. to 35° C. for from 10 hours to 20 hours to obtain a fermented medium comprising a substrate and supernatant; and isolating the supernatant from the substrate and recovering the supernatant to obtain a product comprising active dextran sucrase.

18. A process according to claim 17 wherein the culture medium is incubated at a pH of from 6 to 7.3 and wherein the process further comprises steps of:

adjusting the pH of the supernatant to a pH of from 4.9 to 5.7 to obtain a pH-adjusted product;

storing the pH-adjusted product at a temperature of from 0° C. to 10° C. for from 15 hours to 30 hours to obtain a cooled pH-adjusted product;

treating the cooled pH-adjusted product to obtain a precipitate and a supernatant; and isolating the precipitate from the supernatant and obtaining the precipitate to obtain the active dextran sucrase product.

19. A process according to claim 17 wherein the process further comprises, after isolating and obtaining the precipitated product and prior to the incorporating step, a step of dialyzing the precipitate product.

20. A process according to claim 17 wherein the strain produces, during culturing in DEX medium, a fermented medium which has, upon passage of 100 ml of the fermented medium through a gravity viscometer having a diameter of 25 mm for determination of viscosity in seconds, a viscosity of at least 12 seconds.

21. A process according to claim 17 wherein the strain does not ferment lactose.

22. A process according to claim 17 wherein the strain is selected from the group consisting of isolated bacteria strain *Leuconostoc mesenteroides* ssp. *cremoris* CNCM I-1692 and isolated bacteria strain *Leuconostoc mesenteroides* ssp. *cremoris* CNCM I-1693.

23. A process according to claim 17 wherein the culture medium comprises the sucrose in an amount of at least 2% by weight.

* * * * *